United States Patent
Guta et al.

(10) Patent No.: US 10,898,139 B2
(45) Date of Patent: Jan. 26, 2021

(54) SPINE CONSTRUCTION FOR BASKET CATHETER

(71) Applicant: Biosense Webster (Israel) Ltd., Yokneam (IL)

(72) Inventors: Alexandru Guta, Chino Hills, CA (US); Marius Petrulis, Altadena, CA (US); Ronald Lin, La Puente, CA (US); Jon Davis, Riverside, CA (US); David Johnson, Monrovia, CA (US); Patrick O'Fallon, Toluca Lake, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1027 days.

(21) Appl. No.: 15/172,530

(22) Filed: Jun. 3, 2016

(65) Prior Publication Data

US 2017/0347959 A1    Dec. 7, 2017

(51) Int. Cl.
*A61B 5/00* (2006.01)
*A61B 5/042* (2006.01)
*A61B 18/14* (2006.01)
*A61B 17/00* (2006.01)
*A61B 18/00* (2006.01)

(52) U.S. Cl.
CPC .......... *A61B 5/6858* (2013.01); *A61B 5/0422* (2013.01); *A61B 18/14* (2013.01); *A61B 2017/00053* (2013.01); *A61B 2017/00526* (2013.01); *A61B 2017/00867* (2013.01); *A61B 2018/00267* (2013.01); *A61B 2562/125* (2013.01)

(58) Field of Classification Search
CPC ................ A61B 5/6858; A61B 5/0422; A61B 2017/00526; Y10T 29/49174; Y10T 29/49117; Y10T 29/49002

USPC ........................................................ 29/857
See application file for complete search history.

(56) References Cited

U.S. PATENT DOCUMENTS 4,280,511 A    7/1981  O'Neill
5,423,881 A    6/1995  Breyen et al.
(Continued)

FOREIGN PATENT DOCUMENTS

EP    0329112 A1    8/1989
WO    96/39966 A1   12/1996

OTHER PUBLICATIONS

European Search Report and Written Opinion for European Application No. 17174355.2, dated Nov. 10, 2017.

*Primary Examiner* — Peter Dungba Vo
*Assistant Examiner* — Azm A Parvez
(74) *Attorney, Agent, or Firm* — Dergosits & Noah LLP; Todd A. Noah (57) ABSTRACT

A spine of an electrode assembly is constructed by simultaneously deploying a plurality of individual bobbins of lead wire radially around the longitudinal axis of a polymeric tube. A free end of lead wire from each bobbin is electrically connected to a respective electrode and the electrodes are sequentially installed from a distal first location on the polymeric tube to a proximal location. Each lead wire may be helically wound around the polymeric tube between the electrode to which the lead wire is electrically connected and a proximally adjacent electrode, such that each lead wire between adjacent pairs of electrodes has an alternating direction of winding.

13 Claims, 5 Drawing Sheets

(56) References Cited

U.S. PATENT DOCUMENTS

| | | | |
|---|---|---|---|
| 5,476,495 A * | 12/1995 | Kordis | A61B 5/0422 |
| | | | 607/122 |
| 5,555,618 A | 9/1996 | Winkler | |
| 5,591,142 A | 1/1997 | Van Erp et al. | |
| 5,772,590 A | 6/1998 | Webster | |
| 5,855,552 A * | 1/1999 | Houser | A61M 25/0009 |
| | | | 600/374 |
| 6,032,061 A | 2/2000 | Koblish | |
| 6,064,905 A | 5/2000 | Webster | |
| 6,456,863 B1 | 9/2002 | Levin et al. | |
| 6,748,255 B2 | 6/2004 | Fuimaono | |
| 6,757,970 B1 | 7/2004 | Kuzma et al. | |
| 6,961,602 B2 | 11/2005 | Fuimaono | |
| 6,973,340 B2 | 12/2005 | Fuimaono | |
| 7,993,481 B2 | 8/2011 | Hastings et al. | |
| 8,677,619 B2 | 3/2014 | Dye et al. | |
| 2006/0200217 A1 | 9/2006 | Wessman | |
| 2015/0342532 A1 | 12/2015 | Basu et al. | |
| 2016/0158490 A1* | 6/2016 | Leeflang | A61M 25/005 |
| | | | 604/527 |

\* cited by examiner

SPINE CONSTRUCTION FOR BASKET CATHETER

FIELD OF THE PRESENT DISCLOSURE

This invention relates to electrophysiologic (EP) catheters for mapping and/or ablation in the heart, in particular, to spines used to form a basket-shaped electrode assembly and systems and methods for constructing them.

BACKGROUND

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector. Mapping the activation front and conduction fields aids the physician in identifying and diagnosing abnormalities, such as ventricular and atrial tachycardia and ventricular and atrial fibrillation, which may result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated so as to restore the normal function of the heart insofar as is possible. As an illustration, cardiac arrhythmias including atrial fibrillation, may occur when regions of cardiac tissue abnormally conduct electric signals to adjacent tissue, thereby disrupting the normal cardiac cycle and causing asynchronous rhythm. Procedures for treating arrhythmia include disrupting the origin of the signals causing the arrhythmia, as well as disrupting the conducting pathway for such signals, such as by forming lesions to isolate the aberrant portion. Thus, by selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

A number of advantages may be obtained by providing a catheter having multiple electrodes to allow for mapping larger regions and/or for creating a plurality of lesions either simultaneously or without the need to reposition the catheter. One suitable configuration is a basket-shaped electrode assembly, such as described in commonly assigned U.S. Pat. Nos. 5,772,590, 6,748,255 and 6,973,340, the entire disclosures of each are incorporated herein by reference. Basket catheters typically have an elongated catheter body and a basket-shaped electrode assembly mounted at the distal end of the catheter body. The basket assembly has proximal and distal ends and comprises a plurality of spines connected at their proximal and distal ends. Other electrode assembly configuration may be employed that also feature one or more spines having multiple electrodes. For example, commonly assigned U.S. Pat. No. 6,961,602, which is hereby incorporated by reference, discloses a multiray electrode assembly having two or more spines, attached at their proximal with free distal ends.

Each spine comprises at least one electrode, and more commonly, several. Correspondingly, each electrode requires its own lead to conduct the electrical signals received at the electrodes through the catheter for recording and processing by instrumentation coupled to the catheter. Conventionally, the spines may be formed using a core substrate, such as a shape memory wire, coaxially disposed within a polymeric tube. The multiplicity of leads may be embedded in the polymeric tube, providing insulation and protection. However, each lead must be connected to its respective electrode, which represents a significant investment of time and labor as well as being subject to a high failure rate. For example, as each ring electrode is installed, an opening in the outer layer of the polymeric tube is created to provide access to the lead. The end of the lead is then teased out from the polymeric tube and prepared for connection to the electrode. This may include sandblasting the end of the lead or performing another operation to remove the epoxy insulation and to clean the lead. The electrode is then welded or soldered to the lead and crimped onto the polymeric tube.

The sequence of steps of isolating each lead, cleaning it and securing it to the electrode must be repeated for each electrode on the spine. To provide a more accurate map, or to access more area with greater resolution, current trends in catheter design call for a relatively high density of electrodes. For example, a typical spine may have sixteen electrodes or more, necessitating a corresponding number of repetitions of the electrode connection process. The leads may be of relatively small gauge, such as 0.0012 in, making them fragile and susceptible to breakage. Should any lead be damaged during electrode installation, the entire spine and all the effort expended to that point is wasted. The costs associated with the time and labor required to connect each electrode are significant and the polymeric tubing with embedded wires represents a substantial portion of the material costs associated with a basket-shaped electrode assembly.

As noted above, each spine may have a core substrate that is configured to allow the electrode assembly to assume a desired configuration when deployed. In some embodiments, this may include the use of shape memory materials that may exhibit a preformed configuration. It has been observed that the polymeric tubing with embedded wires tends to interfere with the spine assuming its desired shape when deployed. Generally, the polymeric tubing tends to constrain the spine in a more linear configuration, keeping the spine from bowing outwards to the desired degree. Further, the embedded wires exacerbate this effect, by functioning like braided reinforcements. For example, a basket-shaped electrode assembly may be intended to assume a relatively spherical configuration when deployed, but the polymeric tubing with embedded wires may provide resistance that causes the electrode assembly to be ellipsoidal instead. Furthermore, the leads may be wound around the longitudinal axis in a given direction and, in turn, may impart a force that tends to laterally deflect the spine when the electrode assembly is deployed in its expanded configuration. As a result, the deployed assembly may exhibit an undesirable asymmetry.

In light of the above context, it would be desirable to provide a spine construction that is more fault tolerant, such that a failure with one electrode need not affect the already installed electrodes or the electrodes still to be connected. Likewise, it would be desirable to provide systems and methods for facilitating the connection and installation of electrodes when manufacturing the spine. Further, it would be desirable to minimize the resistance offered by the polymeric tubing to allow the spine to more closely assume its intended shape when deployed. Still further, it would also be desirable to provide a spine construction to facilitate the formation of a symmetrical configuration when deployed. The techniques of this disclosure as described in the following materials satisfy these and other needs.

SUMMARY

The present disclosure is directed to a method for constructing a spine of an electrode assembly for an electrophysiologic catheter. The method may involve stabilizing a polymeric tube along a longitudinal axis, providing a number of electrodes, simultaneously deploying a plurality of individual bobbins of lead wire corresponding to the number of electrodes radially around the longitudinal axis, wherein a free end of lead wire from each bobbin is electrically connected to a respective electrode and sequentially installing the electrodes from a distal first location on the polymeric tube to a proximal location.

In one aspect, the lead wire of each electrode may be helically wound around the polymeric tube between the electrode to which the lead wire is electrically connected and a proximally adjacent electrode, such that each lead wire between adjacent pairs of electrodes has an alternating direction of winding. Each lead wire may be longitudinally aligned with the longitudinal axis along the polymeric tube proximal of the proximally adjacent electrode.

In one aspect, tension may be applied to the lead wire of each bobbin during electrode installation.

In one aspect, the lead wires between adjacent electrodes may be covered with a polymeric material following electrode installation.

In one aspect, the individual bobbins of lead wire may be deployed by a holder that rotates about the longitudinal axis and the lead wires may be wound around themselves proximally of the polymeric tube following electrode installation.

In one aspect, the electrical connection between the free end of lead wire from each bobbin and its respective electrode may be provided by securing the lead wire to a ring electrode and threading each ring electrode over the polymeric tube in sequence. Each ring electrode may be installed by crimping the ring electrode to the polymeric tube at a desired location.

In one aspect, the electrical connection between the free end of lead wire from each bobbin and its respective electrode may be provided by securing the lead wire perpendicularly to a strip of electrode material and forming a ring electrode during installation by wrapping the strip of electrode material around the polymeric tube. The strip of electrode material may be folded over a secured portion of the lead wire prior to wrapping the strip of electrode material around the polymeric tube.

This disclosure also includes a spine of an electrode assembly for an electrophysiologic catheter having a flexible core disposed within a lumen of a polymeric tube, wherein the polymeric tube has a number of electrodes and is constructed by stabilizing the polymeric tube along a longitudinal axis, simultaneously deploying a plurality of individual bobbins of lead wire corresponding to the number of electrodes radially around the longitudinal axis, wherein a free end of lead wire from each bobbin is electrically connected to a respective electrode and sequentially installing the electrodes from a distal first location on the polymeric tube to a proximal location.

In one aspect, constructing the spine may also include helically winding the lead wire around the polymeric tube between the electrode to which the lead wire is electrically connected and a proximally adjacent electrode, such that each lead wire between adjacent pairs of electrodes has an alternating direction of winding.

In one aspect, constructing the spine may include securing each lead wire to a ring electrode and threading each ring electrode over the polymeric tube in sequence.

In one aspect, constructing the spine may include securing a lead wire perpendicularly to a strip of electrode material and forming a ring electrode during installation by wrapping the strip of electrode material around the polymeric tube. Constructing the spine may also include folding the strip of electrode material over a secured portion of the lead wire prior to wrapping the strip of electrode material around the polymeric tube.

This disclosure also includes a spine of an electrode assembly for an electrophysiologic catheter having a flexible core disposed within a lumen of polymeric tube, wherein the polymeric tube has a number of electrodes and wherein a lead wire for each electrode is helically wound around the polymeric tube between the electrode to which the lead wire is electrically connected and a proximally adjacent electrode, such that each lead wire between adjacent pairs of electrodes has an alternating direction of winding.

In one aspect, each lead wire may be longitudinally aligned along the polymeric tube proximal of the proximally adjacent electrode.

This disclosure also includes a construction device for a spine of an electrode assembly for an electrophysiologic catheter, wherein the spine has a number of electrodes. The device may include a mandrel for stabilizing a polymeric tube along a longitudinal axis, a plurality of individual bobbins of lead wire corresponding to the number of electrodes and a holder that deploys the plurality of bobbins radially around the longitudinal axis.

In one aspect, the holder may rotate about the longitudinal axis.

In one aspect, the construction device may also include a track that is fixed in relation to the mandrel, wherein the holder is slidably mounted to the track to move along the longitudinal axis relative to the mandrel.

In one aspect, the construction device may also include a tensioner for each of the lead wires.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a," "an" and "the" include plural referents unless the content clearly dictates otherwise.

As noted above, certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, an assembly having multiple spines may deploy an array of electrodes to accurately map this electrical activity.

Further, RF energy may be delivered to selected treatment areas for ablation based therapies, including for example, isolation of a source of irregular electrical signals by blocking electrical conduction. Focal ablations using unipolar devices benefit from targeted delivery of RF energy along with localized feedback of catheter placement, both spatially and with respect to tissue engagement. However, focal ablation procedures typically involve relative long procedure times as a result of the physician needing to stich a series of "quantized" RF ablation to form a lesion having the desired characteristics, such as the creation of a continuous circumferential block which surrounds the ostium of the targeted vein. Additionally, the use of a focal unipolar electrode requires substantial physician skill level augmented with peripheral navigation systems in order to accurately and reliably position the electrodes. Correspondingly, an assembly having multiple spines may deploy an array of electrodes to simultaneously deliver ablation energy at a plurality of locations.

Figure 1:
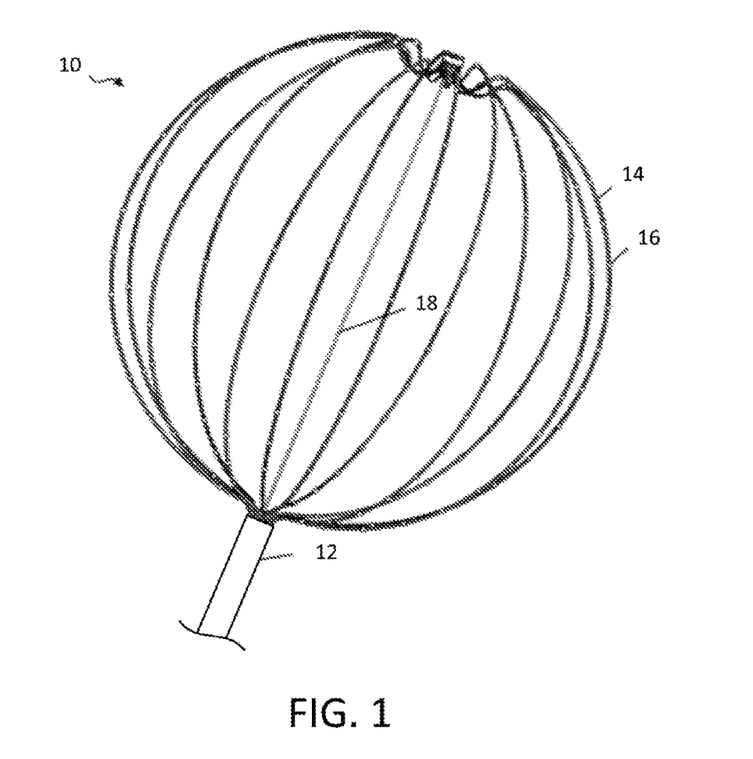
FIG. 1 is a top plan view of a basket-shaped electrode assembly, according to one embodiment.

To provide a context for the disclosure, an exemplary basket-shaped electrode assembly 10 is depicted in FIG. 1. As will be appreciated, the techniques of this disclosure may be applied to any electrode assembly featuring one or more spines, each carrying a plurality of electrodes, which may assume any desired configuration when deployed. In this embodiment, basket-shaped electrode assembly 10 is shown to be disposed at the distal end of an elongated catheter body 12 and includes a plurality of spines 14, each carrying multiple electrodes 16. The proximal portion of the catheter may have a control handle as conventionally used to manipulate the catheter as it is advanced through the patient's vasculature. Likewise, the proximal end also may be configured to provide suitable connections between the electrode leads and the adjunct equipment used to perform the procedure, such as a processor to record and analyze the electrical signals obtained with the electrodes.

Any number of spines 14 may be employed. For example, a basket-shaped electrode assembly having a relatively high density electrode array may have eight, twelve, sixteen or more spines. Depending on the application, fewer spines, such as one or more may be used. Spines 14 may be evenly or unevenly distributed radially. Further, each spine 14 may include multiple electrodes 16, such in the range of ten to twenty electrodes per spine. In other applications, fewer numbers electrodes may be employed as desired. In one illustrative embodiment, the basket-shaped electrode assembly may have sixteen spines with twelve electrodes each to deploy an array of 192 electrodes. Further, the electrodes may be evenly distributed along each spine or may be skewed proximally, centrally or distally to facilitate analysis of the measured electrical signals or to access desired regions of the patient's anatomy. In some embodiments, one or more of electrodes 16 may be configured to deliver radio frequency energy to ablate tissue adjacent the electrode.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle is rotated, the distal end of the catheter body will rotate in a corresponding manner. The outer diameter of the catheter body 12 is not critical, but generally should be as small as possible and may be no more than about 10 french depending on the desired application. Likewise, the thickness of the outer wall is not critical, but may be thin enough so that the central lumen can accommodate a pulling member wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

In basket-shaped electrode assembly 10, the distal ends of spines 14 are secured together and optionally may be attached to a pulling member 18 that is generally coaxial with the catheter body 12 and extends from the proximal end of catheter body 12 through the central lumen. The pulling member 18 is afforded longitudinal movement relative to the catheter body so that it can move the distal ends of the spines 14 proximally relative to the catheter body 12 to radially expand the electrode assembly. The expanded arrangement may have the generally spherical shape shown in FIG. 1, although configurations such as elliptical, ovoid or others may be employed as desired. In some embodiments, spines 14 may have a preshaped expanded configuration that they assume when unconstrained, such as through the use of a shape memory material as noted below, and do not require a pulling member. The proximal ends of spines 14 may be secured at the catheter body 12, so that the distance between the distal and proximal ends of spines 14 shortens when they bow outwards into an expanded arrangement, which may be associated with relative movement of pulling member 18 in the proximal direction.

When in a collapsed arrangement, the spines may be constrained, such as by a guiding sheath, and may be deflected from the collapsed arrangement to the expanded deployed arrangement by withdrawing the guiding sheath and, in some embodiments, imparting sufficient force to pulling member 18. As will be appreciated, in the collapsed arrangement, spines 14 assume a generally linear alignment with the catheter body 12 to minimize the outer diameter for insertion within and withdrawal from the patient. In the expanded arrangement, spines 14 of basket-shaped electrode assembly 10 bow outwards. When positioned at a desired location within a patient, assuming an expanded arrangement may bring electrodes 16 into contract or closer proximity with the walls of the chamber or other region in which basket-shaped electrode assembly 10 is positioned. The overall size of basket-shaped electrode assembly 10 may be selected based on the patient's anatomy to provide a close fit to the area of the patient being investigated or treated, such as the right or left atria.

Figure 2:
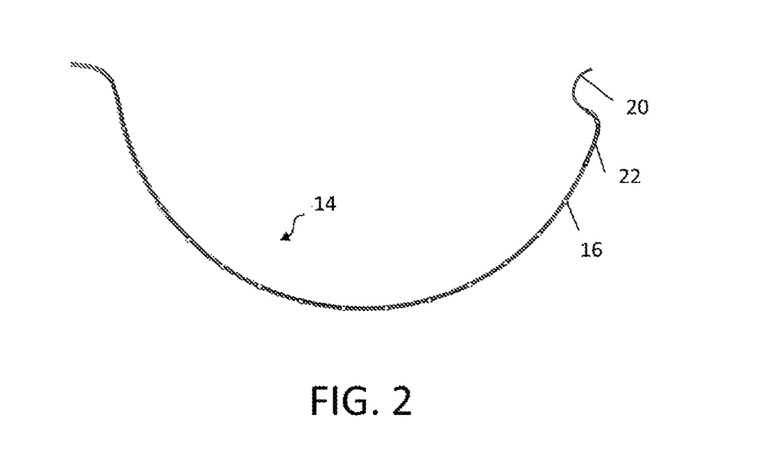
FIG. 2 is a detail view of a spine of a basket-shaped electrode assembly, according to one embodiment.

A single spine 14 is shown in detail in FIG. 2 and may be constructed by employing a substrate material, such as a shape memory material, to form a flexible core 20 that is coaxially disposed within a polymeric tube 22. Electrodes 16 may be configured as ring electrodes and may be secured over polymeric tube 22 as described in further detail below.

Notably, the use of a shape memory material may be used to aid assuming the expanded and collapsed arrangements. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature.

Accordingly, basket-shaped electrode assembly 10 when formed from such materials may have a three dimensional shape that can be easily collapsed to be fed into a guiding sheath and then readily returned to its expanded shape memory configuration upon delivery to the desired region of the patient upon removal of the guiding sheath and/or actuation of pulling member 18. In one exemplary embodiment, a framework comprising some or all the spines 14 may be formed from a nitinol hypotube by laser cutting or other similar techniques, to provide a monolithic framework. Depending on the embodiment, a 3 mm tube having a wall thickness of approximately 8 to 9 mil may be used. Alternative embodiments may employ other materials do not necessarily have shape memory characteristics, but have sufficient resilience to assume the expanded and collapsed arrangements, including metallic materials such as stainless steel or polymeric materials such as polyetheretheketone (PEEK).

Since each spine carries multiple electrodes, a corresponding plurality of leads must be provided to electrically couple the electrodes and provide a connection at the proximal end of the catheter. As discussed above, conventional constructions may employ a "prewired" polymeric tube in which the requisite number of leads are already embedded. This technique results in the time and labor intensive practice of accessing, exposing, preparing and welding each lead to its respective electrode as they are installed over the polymeric tube. There is no practical way to repair a break if one of the lead wires is damaged during electrode installation, requiring the costly prewired polymeric tube to be scrapped and causing a loss of all the time and effort already expended.

Figure 3:
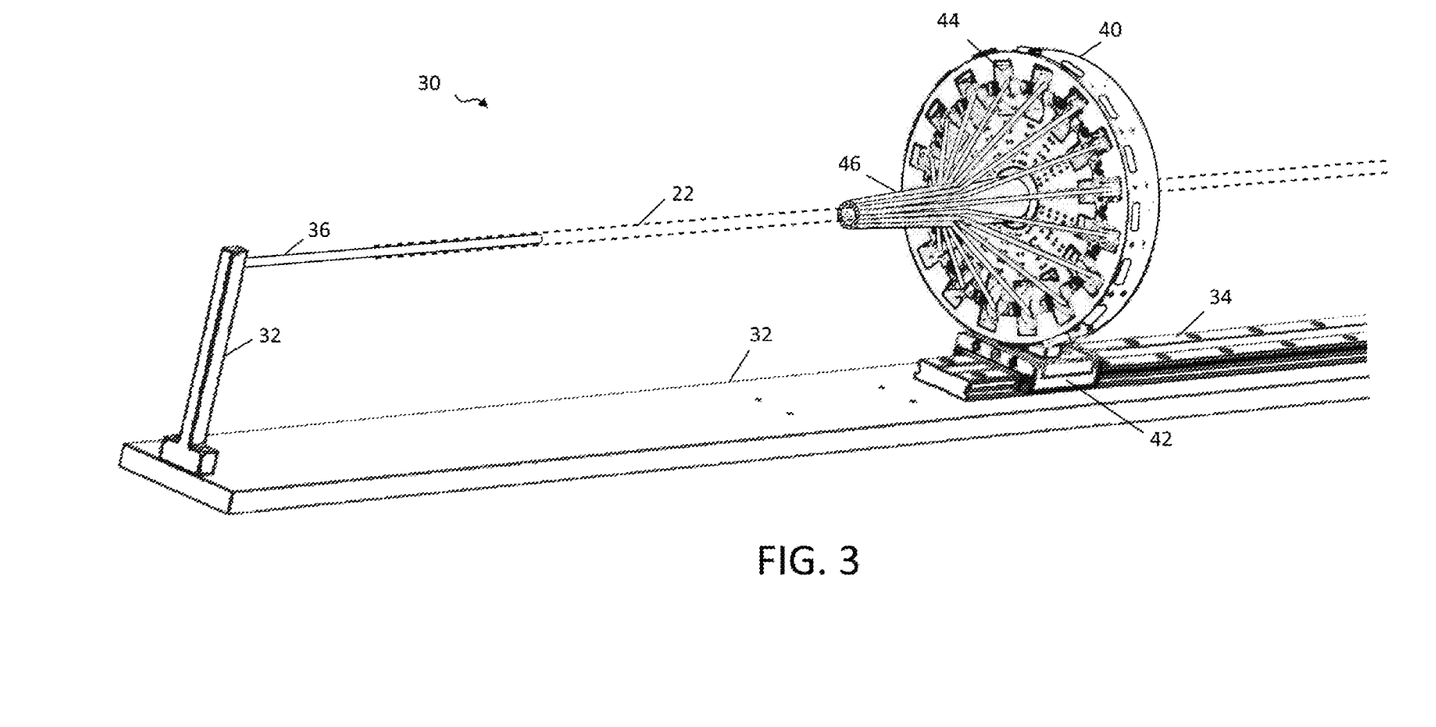
FIG. 3 is a schematic view of a construction device for use when installing electrodes on a polymeric tube, according to one embodiment.

To overcome these drawbacks, as well as providing other advantages that will be noted below, the techniques of this disclosure involve simultaneously providing individual supplies of lead wire for each electrode to be installed on a single spine. As an example and without limitation, one embodiment of a spine construction device 30 is schematically depicted in FIG. 3. A base plate 32 provides mounting for a mandrel support 32 and track 34. In turn, mandrel support 32 positions mandrel 36 that defines a corresponding longitudinal axis. A polymeric tube 22 (shown in phantom) may be disposed over mandrel 36 so that the polymeric tube is stabilized along the longitudinal axis. PEBAX or other similar materials may be used. A bobbin holder 40 is carried by a bracket 42 that is slidably secured to track 34, so that the position of bobbin holder 40 may be adjusted along the longitudinal axis. If desired, bobbin holder 40 may have an axial opening (not shown in this view) aligned with the longitudinal axis to allow it to be advanced over the proximal end of the polymeric tube. Bobbin holder 40 deploys a plurality of bobbins 44, each of which supplies lead wire 46 for electrodes to be mounted on polymeric tube 22. In some embodiments, the lead wire may be monel wire having a diameter of 0.001 inch, although other materials may be used as warranted by the intended application. Generally, the number of bobbins 44 corresponds to the number of electrodes that will be installed per spine, which in this embodiment is sixteen. Accordingly, each bobbin 44 simultaneously supplies lead wire for each electrode being installed. Since each bobbin 44 is independent, if one lead breaks during electrode installation, a fresh length of lead wire may be unspooled from the respective bobbin and secured to its electrode without affecting the other electrodes or lead wires. As shown, bobbins 44 are arranged radially around the longitudinal axis. Bobbin holder 40 may be mounted to bracket 42 in a manner that allows rotation about the longitudinal axis.

Figure 4:
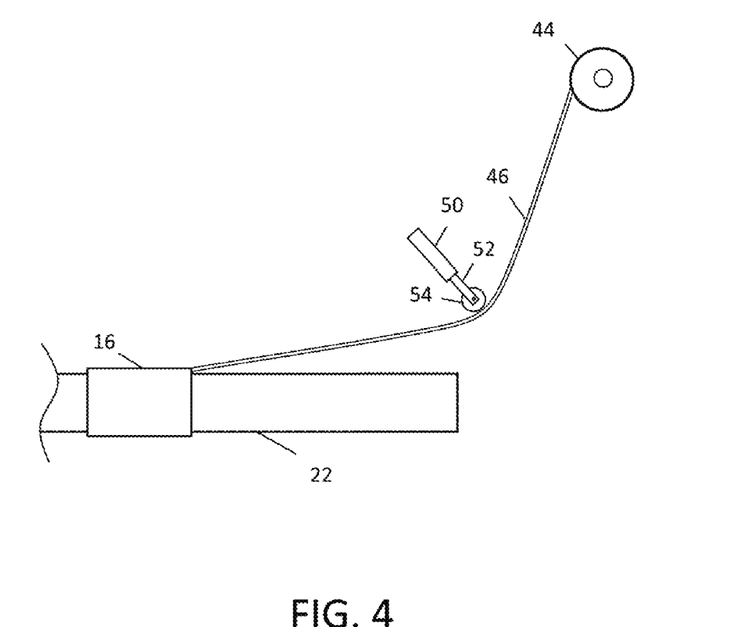
FIG. 4 is a schematic view of a tensioner for a lead wire, according to one embodiment.

It may be desirable to impart a slight tension to the lead wires during the spine construction process to keep the wires properly organized and to help avoid damage. For example, FIG. 4 schematically depicts one suitable arrangement with respect to a single bobbin for clarity, with the understanding a similar mechanism may be provided for each bobbin. As shown, a tensioner body 50 may slidably deploy piston 52 carrying roller 54 that engages lead wire 46. Bobbin 44 may have a brake to prevent the lead wire from unspooling freely. Piston 52 may be biased to slide outwards from tensioner body 50 using a spring, hydraulics or any other suitable mechanism in order to cause lead wire 46 to be under tension when the free end 56 is restrained, such as being secured to an electrode 16 that has been installed on polymeric tube 22. The free ends of lead wires 46 may also be temporarily clamped to a distal section of polymeric tube 22, mandrel 36 and/or mandrel support 32 to allow tension to be applied.

In one aspect, the free end of each lead wire may be secured to an electrode that is already ring shaped. The preshaped ring electrode may have an inner diameter that fits closely over the outer diameter of polymeric tube 22, allowing the longitudinal position of the electrode to be adjusted as desired prior to installation. The spacing between the inner diameter of the ring electrode and the outer diameter of polymeric tube 22 may also allow travel of one or more lead wires. These dimensions allow each the longitudinal position of each ring electrode to be adjusted relative to each other prior to being secured to polymeric tube 22. Lead wire 46 is secured to electrode using any suitable technique that forms an electrical as well as mechanical connection. In some embodiments, the lead wire may be welded to the electrode, but soldering or other functionally equivalent procedures may also be employed. Welding may include preparatory steps such as sandblasting or other cleaning methods, as well as finishing steps, such as buffing or sanding. Following welding, a sequence of ring electrodes may be threaded over polymeric tube 22, with each electrode secured to its respective lead wire. Installation of the ring electrodes may be completed by crimping the electrodes over polymeric tube 22 at desired locations. In some embodiments, a two step crimping process may be employed involving a first crimping operation that fixes the ring electrode at a given longitudinal position, but still allows one or more lead wires to slide between the polymeric tube 22 and the ring electrode so that the position of the other electrodes may be adjusted. After the initial crimp and when the positions of all electrodes on the spine have been established, a secondary crimping process may be performed to complete the installation.

Figure 5:
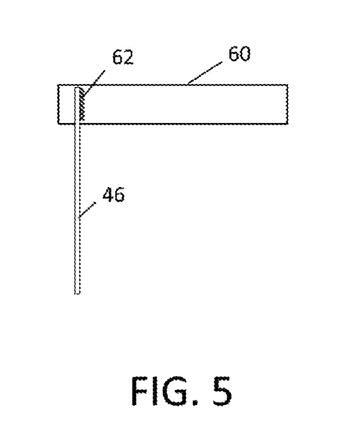
FIG. 5 is a schematic view of a lead wire secured to a strip of electrode material, according to one embodiment.
Figure 6:
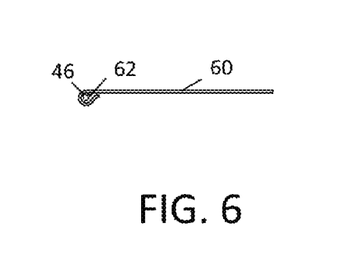
FIG. 6 is an end view of a lead wire secured to a strip of electrode material, according to one embodiment.
Figure 7:
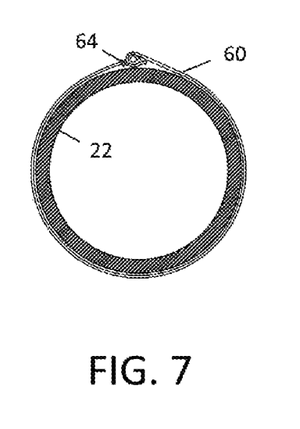
FIG. 7 is a schematic view of a first configuration of wrapped electrode material to form a ring electrode, according to one embodiment.
Figure 8:
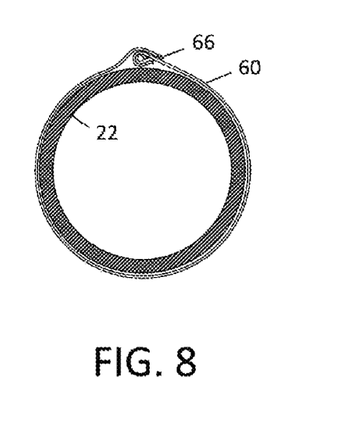
FIG. 8 is a schematic view of a second configuration of wrapped electrode material to form a ring electrode, according to one embodiment.
Figure 9:
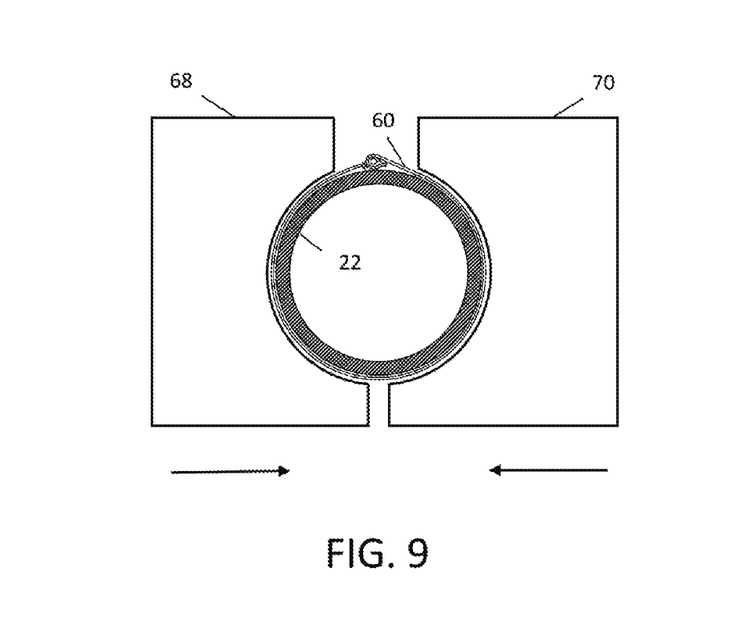
FIG. 9 is a schematic view of complementary dies used to swage wrapped electrode material to form a ring electrode, according to one embodiment.

In another aspect, each electrode 16 may be formed in place. Beginning with a suitably sized strip of electrode material 60 as shown in elevation view FIG. 5, the free end of a lead wire 46 may be secured generally perpendicularly by weld 62, or any other technique as described above, leaving a flap to one side. As an illustration only and without limitation, the dimensions of the strip of electrode material may include a width of approximately 0.025 inch, a length of approximately 0.25 inch and a thickness of approximately 0.001 inch and may be formed from palladium, gold, platinum or other similar metals or alloys. The flap then may be folded over the lead wire 46 and weld 62 as shown in the end view of FIG. 6 to protect the bond and add another degree of mechanical and electrical connection. As will be appreciated, this process may provide a more reliable and durable connection than would be achieved using a spot weld or the like. Next, electrode material 60 may be wrapped around polymeric tube 22 at a desired location to form a ring electrode. As shown in FIG. 7, the strip of electrode material may wrap around polymeric tube 22 so that the end opposite the enfolded lead wire abuts the fold and the ring may be completed by weld 64. Alternatively, as shown in FIG. 8, the strip of electrode material may wrap around polymeric tube 22 so that the end opposite the enfolded lead wire overlaps the fold and the ring may be completed by weld 66 on the other side of the fold. The length of strip 60 may be adjusted depending on which technique is used. The first configuration offers the benefit of reducing the overall diameter of the formed ring electrode while the second configuration may provide more tolerance for the welding operation. One suitable technique for wrapping the strip of electrode material may involve swaging the strip between complementary dies 68 and 70 as schematically indicated in FIG. 9 to increase the consistency of the formed ring electrodes.

Figure 10:
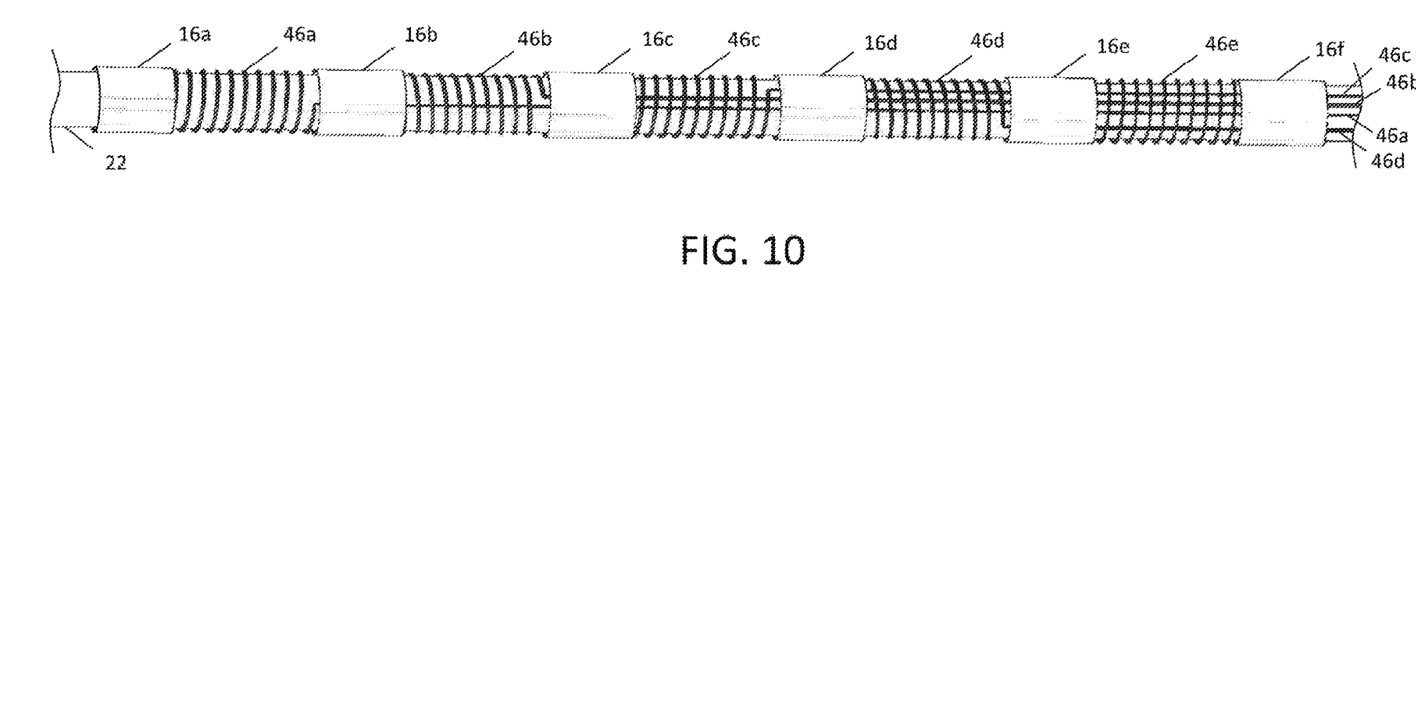
FIG. 10 is a schematic view of the alternating direction of winding of lead wires between adjacent pairs of electrodes, according to one embodiment.

In yet another aspect, the lead wires 46 for each electrode 16 may be helically wound around polymeric tube 22 in alternating directions as schematically shown in FIG. 10. Beginning with the most distal electrode, lead wire 46*a* that is secured to electrode 16*a* may be wound a plurality of times around polymeric tube in one direction, such as either a right hand wrap or a left hand wrap. The wrapping of lead wire 46*a* may terminate at the proximally adjacent electrode, electrode 46*b* in this example, and then extend substantially aligned with the longitudinal axis of polymeric tube 22 to its proximal end. Correspondingly, lead wire 46*b* may be wound around polymeric tube 22 in the opposite direction until reaching the next proximally adjacent electrode, electrode 16*c*. Again, once reaching the proximally adjacent electrode, the lead wire may be longitudinally aligned. Likewise, lead wire 46*c* for electrode 16*c* may be wrapped in the opposite direction as compared to lead wire 46*b*, which is the same direction as lead wire 46*a*. As shown, lead wires 46*d* and 46*e* for electrodes 16*d* and 16*e*, respectively, continue the pattern of alternating winding direction of the lead wire between adjacent pairs of electrodes. The lead wire for electrode 16*f* is not shown in this schematic view for the sake of clarity, but also continues the pattern as do the lead wires for all the remaining electrodes, save for the most proximal electrode. The lead wire for the most proximal electrode may either be wound in an opposite direction for a similar distance or may immediately extend in longitudinal alignment. As desired, each lead wire may be color coded to facilitate identification at the proximal end of the catheter.

By employing alternating winding directions of the lead wires, the resulting polymeric tube may be more flexible than conventional tubing having embedded wires, allowing a spine constructed using the techniques of this disclosure to more readily assume the desired expanded configuration when deployed. Further, alternating the direction of winding may reduce the tendency for a directional force to accumulate as compared to tubing have the lead wires wound in a single direction. Correspondingly, a spine employing such alternating winding may assume a more symmetrical configuration when deployed rather than being skewed in one direction. Still further, winding a lead wire over one or more longitudinally aligned lead wires has the potential to induce a current in the longitudinally aligned lead wires that may manifest as noise in the electric signal measured by the corresponding electrode(s). By alternating the winding direction between each pair of electrodes, any induced currents may substantially cancel each other, reducing noise.

As will be appreciated, spine construction device 30, or a similar device, may be employed while installing electrodes 16 along a polymeric tube 22 according to the principles discussed above. A similar process may be used whether the ring electrodes are preshaped or whether they are formed in place from a strip of electrode material. Similarly, the electrodes may be installed so that their respective lead wires exhibit the alternating winding pattern.

For example, a suitable routine using preshaped ring electrodes may begin by securing the free ends of lead wires 46 from each bobbin 44 to a corresponding electrode 16. Each electrode 16 may then be threaded over polymeric tube 22 in sequence and the polymeric tube mounted over mandrel 36. The lead wire for each electrode is routed through the rings of all the electrodes that are proximal. Tension may be applied to the lead wires as desired to prevent slack from developing and to keep the lead wires organized and aligned with the longitudinal axis. The first electrode threaded over the polymeric tube becomes the most distal electrode. It may be slid along polymeric tube 22 until positioned at the desired location. Prior to crimping, the electrode may be rotated about the longitudinal axis to create the appropriate direction of winding of the associated lead wire. Crimping each electrode completes its installation. These steps may be repeated for each subsequent electrode, with alternating winding directions. Once all electrodes are installed, suitable lengths of the lead wires may be wrapped around themselves to extend from the proximal end of polymeric tube 22 to the proximal end of the catheter. This may be performed by rotating bobbin holder 40 multiple times around the longitudinal axis. All lead wires and ring edges on polymeric tube 22 may be covered with polyurethane, heat shrink PEBAX tubing or other similar materials. Polymeric tube 22 may be placed in an oven to cure the polyurethane or shrink the tubing.

A similar routine may be employed when forming the ring electrodes in place from strips of electrode material. All lead wires are pulled to the distal end of polymeric tube 22 and clamped. A first lead wire is then cut to appropriate length, secured to strip of electrode material 60 and wound around polymeric tube 22 in a first direction. The strip of electrode material 60 may then be wrapped, swaged and welded to form a ring electrode at the desired location. The steps are repeated for each successive electrode in the proximal direction, with the ring electrodes formed around polymeric tube 22 and any longitudinally aligned lead wires from more distally positioned electrodes. The other aspects of the routine may be similar to those described above.

Whether using preshaped ring electrodes or forming ring electrodes in place, these techniques allow a damaged lead wire to be easily replaced without affecting the already installed electrodes. For example, if a lead wire breaks or is damaged during the welding or installation process, a suitable length of new wire may be unspooled from the corresponding bobbin 40. The free end of the lead wire may be secured to a ring electrode or strip of material depending on the technique being used, and construction of the spine may continue. As necessary, the free end of the new length of lead wire may be threaded through any proximal ring electrodes prior to being welded to a replacement ring electrode.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for constructing a spine of an electrode assembly for an electrophysiologic catheter comprising:
stabilizing a polymeric tube along a longitudinal axis;
providing a number of electrodes;
simultaneously deploying a plurality of individual bobbins of lead wire corresponding to the number of electrodes radially around the longitudinal axis of the polymeric tube, wherein a free end of lead wire from each bobbin is electrically connected to a respective electrode;
installing the electrodes sequentially from a distal first location on the polymeric tube to a proximal location; and
winding each lead wire helically around the polymeric tube between the electrode to which the lead wire is electrically connected and a proximally adjacent electrode, the winding of each of the lead wires is such that each lead wire between adjacent pairs of electrodes has an alternating direction of winding.

2. The method of claim 1, wherein each lead wire is longitudinally aligned with the longitudinal axis along the polymeric tube proximal of the proximally adjacent electrode.

3. The method of claim 1, further comprising applying tension to the lead wire of each bobbin during electrode installation.

4. The method of claim 1, further comprising covering lead wires between adjacent electrodes with a polymeric material.

5. The method of claim 1, wherein the individual bobbins of lead wire are deployed by a holder that rotates about the longitudinal axis, further comprising winding the lead wires around themselves proximally of the polymeric tube following electrode installation.

6. The method of claim 1, further comprising providing the electrical connection between the free end of lead wire from each bobbin and its respective electrode by securing the lead wire to a ring electrode and threading each ring electrode over the polymeric tube in sequence.

7. The method of claim 6, further comprising installing each ring electrode by crimping the ring electrode to the polymeric tube at a desired location.

8. The method of claim 1, further comprising providing the electrical connection between the free end of lead wire from each bobbin and its respective electrode by securing the lead wire perpendicularly to a strip of electrode material and forming a ring electrode during installation by wrapping the strip of electrode material around the polymeric tube.

9. The method of claim 8, further comprising folding the strip of electrode material over a secured portion of the lead wire prior to wrapping the strip of electrode material around the polymeric tube.

10. The spine of claim 8, wherein constructing the spine further comprises folding the strip of electrode material over a secured portion of the lead wire prior to wrapping the strip of electrode material around the polymeric tube.

11. A spine of an electrode assembly for an electrophysiologic catheter comprising a flexible core disposed within a lumen of a polymeric tube, wherein the polymeric tube has a number of electrodes and is constructed by:
- stabilizing the polymeric tube along a longitudinal axis;
- simultaneously deploying a plurality of individual bobbins of lead wire corresponding to the number of electrodes radially around the longitudinal axis of the polymeric tube, wherein a free end of lead wire from each bobbin is electrically connected to a respective electrode; and
- sequentially installing the electrodes from a distal first location on the polymeric tube to a proximal location, and
- winding each lead wire helically around the polymeric tube between the electrode to which the lead wire is electrically connected and a proximally adjacent electrode, the winding of each of the lead wires is such that each lead wire between adjacent pairs of electrodes has an alternating direction of winding.

12. The spine of claim 11, wherein constructing the spine further comprises securing each lead wire to a ring electrode and threading each ring electrode over the polymeric tube in sequence.

13. The spine of claim 11, wherein constructing the spine further comprises securing a lead wire perpendicularly to a strip of electrode material and forming a ring electrode during installation by wrapping the strip of electrode material around the polymeric tube.

* * * * *